US010088494B2

(12) United States Patent
Provencher et al.

(10) Patent No.: US 10,088,494 B2
(45) Date of Patent: Oct. 2, 2018

(54) METHOD AND SYSTEM FOR MICROFLUIDIC SAMPLE ANALYSIS

(71) Applicant: PerkinElmer Health Sciences, Inc., Waltham, MA (US)

(72) Inventors: Laurel Provencher, Hopkinton, MA (US); Jingjing Wang, Hopkinton, MA (US); I-Jane Chen, Ridgewood, NJ (US); David Weinberger, Hopkinton, MA (US); Wael Yared, Hopkinton, MA (US)

(73) Assignee: PERKINELMER HEALTH SCIENCES, INC., Waltham, MA (US)

( * ) Notice: Subject to any disclaimer, the term of this patent is extended or adjusted under 35 U.S.C. 154(b) by 17 days.

(21) Appl. No.: 15/005,647

(22) Filed: Jan. 25, 2016

(65) Prior Publication Data
US 2017/0212017 A1 Jul. 27, 2017

(51) Int. Cl.
G01N 35/00 (2006.01)
G01N 15/06 (2006.01)
G01N 25/00 (2006.01)
G01N 15/08 (2006.01)

(52) U.S. Cl.
CPC ........... *G01N 35/00693* (2013.01); *G01N 2035/00702* (2013.01)

(58) Field of Classification Search
CPC .................... G01N 35/00; G01N 15/06
USPC ....... 422/68.1; 436/43; 700/266; 702/22, 23, 702/30, 32, 85, 104
See application file for complete search history.

(56) References Cited

U.S. PATENT DOCUMENTS

| 6,495,369 | B1 | 12/2002 | Kercso et al. | |
|---|---|---|---|---|
| 7,316,801 | B2 | 1/2008 | Kercso et al. | |
| 7,888,125 | B2 | 2/2011 | Gibbons et al. | |
| 2005/0130292 | A1* | 6/2005 | Ahn | A61B 5/14532 435/287.1 |
| 2005/0249633 | A1* | 11/2005 | Blatt | B01L 3/5027 422/400 |
| 2005/0255600 | A1* | 11/2005 | Padmanabhan | B01L 3/502715 436/63 |
| 2006/0019319 | A1* | 1/2006 | Billadeau | G01N 33/523 435/7.21 |
| 2006/0257941 | A1* | 11/2006 | McDevitt | B01L 3/502715 435/7.2 |
| 2006/0264781 | A1* | 11/2006 | Gibbons | A61B 5/1411 600/583 |
| 2007/0166195 | A1* | 7/2007 | Padmanabhan | B01L 3/502715 422/68.1 |

(Continued)

OTHER PUBLICATIONS

PerkinElmer, Inc., "Antibody Analysis using microfluidic technology in high throughput Quality by Design Experiments", LabChip GXII Touch Antibody Analysis, Copyright © 2013-2014, PerkinElmer, Inc. All rights reserved, pp. 1-5.

(Continued)

*Primary Examiner* — Brian J. Sines
(74) *Attorney, Agent, or Firm* — Day Pitney LLP

(57) ABSTRACT

Methods and systems for reducing the run-to-run variability in measurement results obtained by a sample analysis system. The method and system utilize data from previous sample runs to optimize analysis parameters for future test runs. The methods and systems are particularly suitable for microfluidic sample analysis.

19 Claims, 10 Drawing Sheets

(56) References Cited

U.S. PATENT DOCUMENTS

2007/0224084 A1* 9/2007 Holmes ................ A61B 5/1411
422/68.1

OTHER PUBLICATIONS

PerkinElmer, Inc., "Low MW Protein Assay User Guide", For LabChip GXII Touch, © Copyright 2014-2015 PerkinElmer, Inc. All rights reserved, pp. 1-34.

* cited by examiner

METHOD AND SYSTEM FOR MICROFLUIDIC SAMPLE ANALYSIS

FIELD

The technology described herein is in the field of sample analysis and measurement methods and systems. In particular, the technology described herein relates to sample analysis and measurement methods and systems that utilize microfluidics for biomolecular separation and quantitation.

BACKGROUND

The use of microfluidics in the analysis and quantitation of biological and chemical samples is well known. One such use involves a system that utilizes a microfluidic chip (sometimes referred to as a "lab-on-a-chip") to obtain one or more samples, to process the sample(s) for measurement, and then to assess the composition of the sample using, for example, spectrophotometry or optical tracking of radioactive or fluorescent markers previously placed in the samples. The microfluidic chip typically includes a number of wells into which dyes and reagents are deposited for interaction with the samples. The wells are linked via microchannels to a separation microchannel through which the samples are drawn for analysis. Samples are typically provided as a group on a multi-well sample plate, which are then loaded (or "sipped") in series onto the chip for combination with reagents and/or dyes and then analysis by the system.

One advantageous application of microfluidics is the electrophoretic analysis of proteins in a biological sample. In this technique, an electrical field is applied to a sample which, in some cases, has been dyed and denatured. The electrical field causes molecules of different types to separate due to the difference with which each type of molecule interacts with the electrical field. For example, different types of proteins have different molecular sizes, so different types of proteins will travel through a material (such as a gel) at different rates depending on their sizes due to the force of the electric field. The proteins, thus separated, can be identified and their attributes measured.

Microfluidic systems are extremely precise measurement tools, and those of skill in the art have occasionally encountered problems with variation in the results of measurements of samples using microfluidics. It has been found that minor fluctuations in the parameters of analysis have a profound effect on the repeatability of the analysis. For example, fluctuations in the features of one microfluidic chip compared to another chip intended to be identical can cause unwanted variation in measurement results. Such fluctuations can include variations in the dimensions of the microchannels. Fluctuations in the attributes of the required reagents can also cause unwanted variations. These can include variations in the dye fluorescence and concentration of the reagents. Similarly, there can also be fluctuations in the test conditions that cause variations in the measured results. These include the power of the laser used to illuminate the sample, the focus position of the laser, and the volume of sample or reagent injected for analysis. Each of the foregoing, and many others not listed, can affect the run-to-run variation in the measurement signal of a microfluidics analysis.

Thus, there is a need in the art to improve the consistency of measured results across multiple runs from a microfluidic system and measurement method. It is further desired that such an improvement be implemented with minimal disruption to currently-employed measurement processes and with minimal cost to the manufacturer and user of the relevant test equipment. Further, it is desired that such improvements be adaptable for use in the context of each of the many possible causes of significant run-to-run variations.

SUMMARY

The technology described herein includes systems and methods that use real-time multivariable analyses and adjustment of operating conditions in order to reduce variability in reported sample analysis results. It may be applied to multiple types of sample analysis techniques, including microfluidic analyses of biomolecules or cells, including, but not limited to, electrophoretic separations of proteins and nucleic acids. The operating conditions are determined based on the measured signals from the previous sample runs under starting conditions. Examples of measured signals are fluorescence reading from biomolecules (protein or other) and measured currents or voltages. Examples of operating/controlling variables of microfluidic chips are imposed voltages and/or currents and/or pressures in supply wells, detector position or imposed times of various steps.

According to the technology described herein, system software is adapted to optimize the analysis parameters that generate a protein signal, or other reported data, before running the test samples. During the pre-test sample processing steps, calibration standard sample(s) are run and analyzed. The software records calibration standard background and protein signals, and optimizes one or more analysis parameters including, for example, the destain via changing the current and/or voltage through the destain channels. When the expected result is seen, the optimized script with correct parameters (like the destain ratio setting) is then stored in the memory and replaces the default script for the real run.

According to a first embodiment of the technology described herein, a method for analyzing a sample is provided, comprising the steps of: A) analyzing a calibration sample using a set of analysis parameters, the calibration sample having an expected value of a first attribute; B) calculating a measured value of the first attribute based at least in part on the analysis of step A); C) comparing the measured value to the expected value to determine whether the measured value varies from the expected value by more than a threshold amount; D) if the measured value varies from the expected value by more than the threshold amount, then 1) adjusting at least one of the set of analysis parameters to create an adjusted set of analysis parameters; 2) performing steps A)-D) iteratively using the adjusted set of analysis parameters until the measured value varies from the expected value by less than the threshold amount; E) if the measured value varies from the expected value by less than the threshold amount, then analyzing a test sample using the first set of analysis parameters.

In some embodiments, the step of A) analyzing a calibration sample further comprises the steps of: 1) sipping the calibration sample into a channel of a microfluidic chip; 2) drawing the calibration sample through a sieving matrix and mixing the calibration sample with at least one of a dye and a surfactant; and 3) illuminating the calibration sample with excitation radiation. In some embodiments, the calibration sample comprises a protein and step A) of analyzing a calibration sample further comprises the steps of: 4) calculating a ratio of an amount of voltage and/or electric current to be applied to a well containing a destain material to an amount of voltage and/or electric current to be applied to draw the calibration sample through the sieving matrix; and 5) diluting the mixture of the calibration sample and at least one of the dye and surfactant by applying the ratio of voltages and/or electric currents.

In some embodiments, the step D)1) of adjusting at least one of the set of analysis parameters further comprises adjusting the ratio of an amount of voltage and/or electric current to be applied to a well containing the destain material to an amount of voltage and/or electric current to be applied to draw the calibration sample through the sieving matrix. In some embodiments, the first attribute is the purity of the calibration sample and the expected value is expressed as a percentage. In some embodiments, the step C) of comparing the measured value to the expected value further comprises the steps of: 1) calculating the percent purity of the calibration sample to obtain the measured value; and 2) subtracting the measured value from the expected value to obtain a value difference.

In some embodiments, the variation between the measured value and the expected value is determined to be below the threshold amount when the absolute value of the value difference is less than about 5% of the expected value. In some embodiments, the step D)2) of performing steps A)-D) iteratively further comprises the step of i) adjusting the ratio by about 0.25 on each iteration of the performance of steps A)-D).

In some embodiments, the method further comprises the step of F) calculating, based on the electric resistance and expected mobility for a standard material for at least one channel on the microfluidic chip, a baseline ratio of an amount of voltage and/or electric current to be applied to a well containing the destain material to an amount of voltage and/or electric current to be applied to draw the calibration sample through the sieving matrix.

In some embodiments, the step of A) analyzing a calibration sample further comprises the steps of: 1) sipping the calibration sample into a channel of a microfluidic chip; 2) mixing the calibration sample with a reagent drawn from at least two reagent wells; 3) drawing the calibration sample through a sieving matrix; and 4) illuminating the calibration sample with excitation radiation. In some embodiments, the step A)2) of mixing the calibration sample with a reagent further comprises the steps of: a) calculating an amount of the reagent to mix with the calibration sample; b) calculating a ratio of an amount of voltage and/or electric current to be applied to a well containing the reagent at a first concentration to an amount of voltage and/or electric current to be applied to a well containing the reagent at a second concentration, wherein the second concentration is different from the first concentration, wherein the ratio is sufficient to mix the calculated amount of reagent with the calibration sample; and c) mixing the reagent and calibration sample by applying the ratio of voltage and/or electric currents. In some embodiments, the step D)1) of adjusting at least one of the set of analysis parameters further comprises adjusting the ratio of an amount of voltage and/or electric current to be applied to a well containing the reagent at a first concentration to an amount of voltage and/or electric current to be applied to a well containing the reagent at a second concentration.

According to a second embodiment of the technology described herein, a system for analyzing a sample is provided, comprising: a detection system adapted to analyze material samples and to provide analysis data associated with each sample; at least one processor; at least one computer-readable medium; data stored on the at least one computer-readable medium comprising a baseline set of analysis parameters for use by the detection system; software stored in the computer-readable medium and programmed to execute on the at least one processor. The software includes instructions to: calculate a measured value of a first attribute of a calibration sample based at least in part on analysis data received from the detection system; compare the measured value to an expected value of the first attribute of the calibration sample to determine whether the measured value varies from the expected value by more than a threshold amount; adjust at least one of the baseline set of analysis parameters so as to create and to store in the at least one computer-readable medium an adjusted set of analysis parameters in the event that the measured value varies from the expected value by more than the threshold amount; prompt a user of the system to initiate analysis of the calibration sample using the adjusted set of analysis parameters; and prompt a user of the system to initiate analysis of a test sample using one of the baseline set of analysis parameters or the adjusted set of analysis parameters.

In some embodiments, the system further comprises: a plate holder for receiving a sample plate and a chip holder for receiving a microfluidic chip, the chip having a sipper through which a sample from the sample plate can be drawn, at least one channel in fluid communication with the sipper, and a plurality of wells. In some embodiments, the detection system further comprises: a sipper actuation element adapted to draw the sample from the sample plate through the sipper and into the at least one channel; a loading well actuation element adapted to apply a voltage and/or electric current to at least one well containing at least one of a dye material and a surfactant; a destain well actuation element adapted to apply a voltage and/or electric current to a destain well containing destain material; a separation channel well actuation element adapted to apply a voltage and/or electric current to at least one well so as to draw the sample through a sieving matrix in a separation channel; and an illuminating element for exposing the sample to an excitation radiation.

In some embodiments, the software stored in the computer-readable medium further includes instructions to: calculate a ratio of an amount of voltage and/or electric current to be applied by the destain well actuation element to an amount of voltage and/or electric current to be applied by the separation channel well actuation element to create a concentration gradient and allow diffusion-driven dilution of the mixture of the calibration sample and the dye; activate the loading well actuation element to mix the dye and the calibration sample; activate the separation channel well actuation element to draw the calibration sample through the separation channel based at least in part on the calculated ratio; and; and activate the destain well actuation element to dilute the mixture of the calibration sample and the at least one of the dye and the surfactant based at least in part on the calculated ratio. In some embodiments, the software stored in the computer-readable medium further includes instructions to: adjust the ratio based on the result of the comparison of the measured value to the expected value and to store the adjusted ratio as one of the adjusted set of analysis parameters on the computer readable medium.

In some embodiments, the software stored in the computer-readable medium further includes instructions to: calculate a baseline ratio of an amount of voltage and/or electric current to be applied by the destain well actuation element to an amount of voltage and/or electric current to be applied by the separation channel well actuation element for storage with the baseline set of analysis parameters. In some embodiments, the instructions to calculate a baseline ratio include instructions to: calculate an expected mobility for a standard material through the at least one channel; calculate an electric resistance of the at least one channel; calculate a maximum initial ratio of an amount of voltage and/or electric current to be applied by the destain well actuation element to an amount of voltage and/or electric current to be applied by the detection channel well actuation element based on the calculated expected mobility and electrical resistance; calculate a minimum initial ratio of an amount of voltage and/or electric current to be applied by the destain well actuation element to an amount of voltage and/or electric current to be applied by the detection channel well actuation element; and calculate the baseline ratio based on a comparison of a measured value of the first attribute of a standard sample obtained using the maximum initial ratio to a measured value of the first attribute of the standard sample obtained using the minimum initial ratio.

In some embodiments, the system further comprises: a plate holder for receiving a sample plate and a chip holder for receiving a microfluidics chip, the chip having a sipper through which a sample from the sample plate can be drawn, at least one channel in fluid communication with the sipper, and a plurality of wells. In some embodiments, the detection system further comprises: a sipper actuation element adapted to draw the sample from the sample plate through the sipper and into the at least one channel; a first reagent well actuation element adapted to apply a voltage and/or electric current to a first reagent well containing a reagent at a first concentration; a second reagent well actuation element adapted to apply a voltage and/or electric current to a second reagent well containing the reagent at a second concentration, wherein the second concentration is different from the first concentration; a separation channel well actuation element adapted to apply a voltage and/or electric current to a well so as to draw the sample through a sieving matrix in a separation channel; and an illuminating element for exposing the sample to an excitation radiation.

In some embodiments, the software stored in the computer-readable medium further includes instructions to: calculate an amount of the reagent to mix with the sample; calculate a ratio of an amount of voltage and/or electric current to be applied to the first reagent well to an amount of voltage and/or electric current to be applied to the second reagent well sufficient to mix the calculated amount of reagent with the calibration sample; and activate the first reagent well actuation element and the second reagent well actuation element to mix the calculated amount of reagent with the sample. In some embodiments, the software stored in the computer-readable medium further includes instructions to: adjust the ratio based on the result of the comparison of the measured value to the expected value and to store the adjusted ratio as one of the adjusted set of analysis parameters on the computer readable medium.

According to a third embodiment of the technology described herein, a non-transitory computer readable medium with data stored thereon is provided, which comprises instructions for execution by at least one processor to: receive a measured value of a first attribute of a calibration sample calculated based at least in part on analysis data generated using a baseline set of analysis parameters by a detection system adapted to analyze material samples; compare the measured value to an expected value of the first attribute of the calibration sample to determine whether the measured value varies from the expected value by more than a threshold amount; adjust at least one of the baseline set of analysis parameters so as to create an adjusted set of analysis parameters in the event that the measured value varies from the expected value by more than the threshold amount; store the adjusted set of analysis parameters; prompt a user of the detection system to initiate analysis of the calibration sample using the adjusted set of analysis parameters; and prompt a user of the detection system to initiate analysis of a test sample using one of the baseline set of analysis parameters or the adjusted set of analysis parameters.

In some embodiments, the data stored on the computer readable medium further comprises instructions for execution by at least one processor to: calculate a ratio of an amount of voltage and/or electric current to be applied by the destain well actuation element to an amount of voltage and/or electric current to be applied by the separation channel well actuation element to create a concentration gradient and allow diffusion-driven dilution of the mixture of the calibration sample and the dye; activate a loading well actuation element to mix at least one of a dye and a surfactant and the calibration sample in at least one channel of a microfluidic chip; activate a separation channel well actuation element to draw the calibration sample through a separation channel of a microfluidic chip based at least in part on the calculated ratio; and activate a destain well actuation element to dilute the mixture of the calibration sample and at least one of the dye and the surfactant based at least in part on the calculated ratio.

In some embodiments, the data stored on the computer readable medium further comprises instructions for execution by at least one processor to: adjust the ratio based on the result of the comparison of the measured value to the expected value and to store the adjusted ratio as one of the adjusted set of analysis parameters on the computer readable medium.

In some embodiments, the data stored on the computer readable medium further comprises instructions for execution by at least one processor to: calculate an amount of a reagent to mix with the calibration sample; calculate a ratio of an amount of voltage and/or electric current to be applied to a first reagent well containing the reagent at a first concentration to an amount of voltage and/or electric current to be applied to a second reagent well containing the reagent at a second concentration sufficient to mix the calculated amount of reagent with the calibration sample, wherein the second concentration is different from the first concentration; and activate a first reagent well actuation element and a second reagent well actuation element using the ratio.

In some embodiments, the data stored on the computer readable medium further comprises instructions for execution by at least one processor to: adjust the ratio based on the result of the comparison of the measured value to the expected value and to store the adjusted ratio as one of the adjusted set of analysis parameters.

Other aspects of the technology described herein and its particular features and advantages will become more apparent from consideration of the following drawings and accompanying detailed description.

DETAILED DESCRIPTION

The present technology provides systems, devices, and methods for analyzing material samples with improved consistency in the results of such analyses. Embodiments of the technology described herein utilize software to adjust a measurement system's analysis parameters based on the results of calibration standard analysis runs before analysis of the desired test samples. Some embodiments of the technology employ software in connection with user inputs to optimize the analysis parameters prior to the test runs. The technology described herein can be embodied in complete sample testing equipment, individual components thereof, software packages embodied on computer readable media or available for download, and individual specific software modules embodied on computer readable media or available for download for incorporation into a software package loaded in a measurement system.

The following description illustrates the technology that is the subject of the present application by way of example, not by way of limitation of the principles thereof. This description will enable one skilled in the art to make and use the technology and describes several embodiments, adaptations, variations, alternatives, and uses of the technology, including what is presently believed to be the best mode of carrying out the technology. However, this technology may be embodied in several forms and should not be construed as limited to the embodiments set forth herein; rather, these embodiments are provided by way of example so that this disclosure will convey the scope of the technology to those skilled in the art.

Figure 1A:
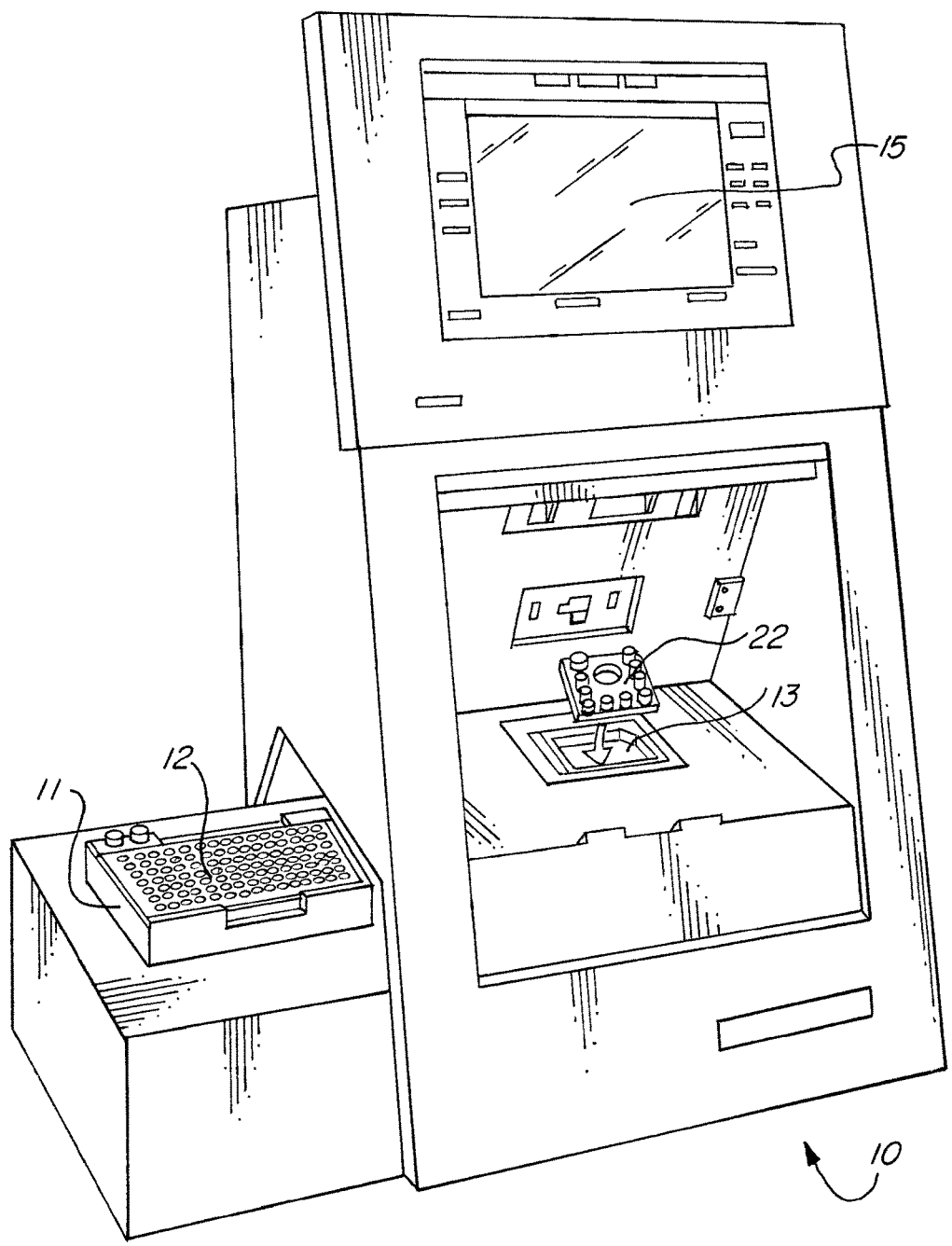
FIG. 1A is a perspective view of an embodiment of a sample analysis system according to the present technology.

FIG. 1A shows a system according to a first embodiment of the present technology. The system 10 is a microfluidics analysis platform that utilizes electrophoretic separation to analyze, or assay, material samples. The system 10 is particularly well adapted to analyzing genomic, protein, biological, and other compound samples. Systems and methods that utilize microfluidics analysis techniques are also described in U.S. Pat. Nos. 6,495,369, 7,316,801, and 7,888,125, the contents of which are hereby incorporated by reference herein.

A variety of assays may be performed using microfluidics according to the subject technology to detect an analyte of interest in a sample. Using labels in an assay as a way of detecting the concentration of the analyte of interest is well known in the art. In some embodiments, labels are detectable by spectroscopic, photochemical, biochemical, immunochemical, or chemical means. For example, useful nucleic acid labels include 32P, 35S, fluorescent dyes, electron-dense reagents, enzymes, biotin, dioxigenin, or haptens and proteins for which antisera or monoclonal antibodies are available. A wide variety of labels suitable for labeling biological components are known and are reported extensively in both the scientific and patent literature, and are generally applicable to the present technology for the labeling of biological components. Suitable labels include radionucleotides, enzymes, substrates, cofactors, inhibitors, fluorescent moieties, chemiluminescent moieties, bioluminescent labels, calorimetric labels, or magnetic particles. Labeling agents optionally include, for example, monoclonal antibodies, polyclonal antibodies, proteins, or other polymers such as affinity matrices, carbohydrates or lipids. Detection proceeds by any of a variety of known methods, including spectrophotometric or optical tracking of radioactive or fluorescent markers, or other methods which track a molecule based upon size, charge or affinity. A detectable moiety can be of any material having a detectable physical or chemical property. Such detectable labels have been well-developed in the field of gel electrophoresis, column chromatography, solid substrates, spectroscopic techniques, and the like, and in general, labels useful in such methods can be applied to the present technology. Thus, a label includes without limitation any composition detectable by spectroscopic, photochemical, biochemical, immunochemical, electrical, optical, thermal, or chemical means.

The system 10 includes sample holder 11 for receiving a sample plate 12. Material samples to be analyzed are provided in appropriate quantities in the sample plate 12. The system 10 also includes a chip holder 13 for receiving a microfluidic chip 22. A microfluidic chip is sometimes referred to as a "lab-on-a-chip" and contains, in some embodiments, a plurality of wells for containing reagents and a plurality of channels that connect the wells.

In some embodiments, a reagent chamber contains about 50 µl to about 1 ml of fluid. In some embodiments, the chamber contains about 100 µl of fluid. The volume of liquid in a reagent chamber will vary depending on the type of assay being run or the sample being analyzed. In some embodiments, the reagents are initially stored dry and liquefied upon initiation of the assay being run on the fluidic device.

Reagents according to the present technology include, without limitation, wash buffers, substrates, gel matrix solutions, dilution buffers, conjugates, enzyme-labeled conjugates, DNA amplifiers, sample diluents, wash solutions, sample pre-treatment reagents including additives such as detergents, polymers, chelating agents, albumin-binding reagents, enzyme inhibitors, enzymes, anticoagulants, red-cell agglutinating agents, antibodies, dyes, hydrophobic dyes, or other materials necessary to run an assay on a fluidic device. An enzyme conjugate can be either a polyclonal antibody or monoclonal antibody labeled with an enzyme, such as alkaline phosphatase or horseradish peroxidase. In some embodiments the reagents are immunoassay reagents.

The channels on the chip generally have a channel cross sectional dimension in the range from about 0.1 µm to about 500 µm, or about the size of a human hair.

The system 10 shown in FIG. 1A also includes a built-in monitor 15. The monitor 15 is, in this embodiment, a touch screen interface by which users of the system 10 interact with the system. Relevant information regarding operation of the system can be provided to the user via the monitor 15, and user instructions can be input to the system 10 via the monitor 15. In other embodiments, a monitor that is separate from the analysis system is provided along with other input devices such as a keyboard and mouse (not shown).

Figure 1B:
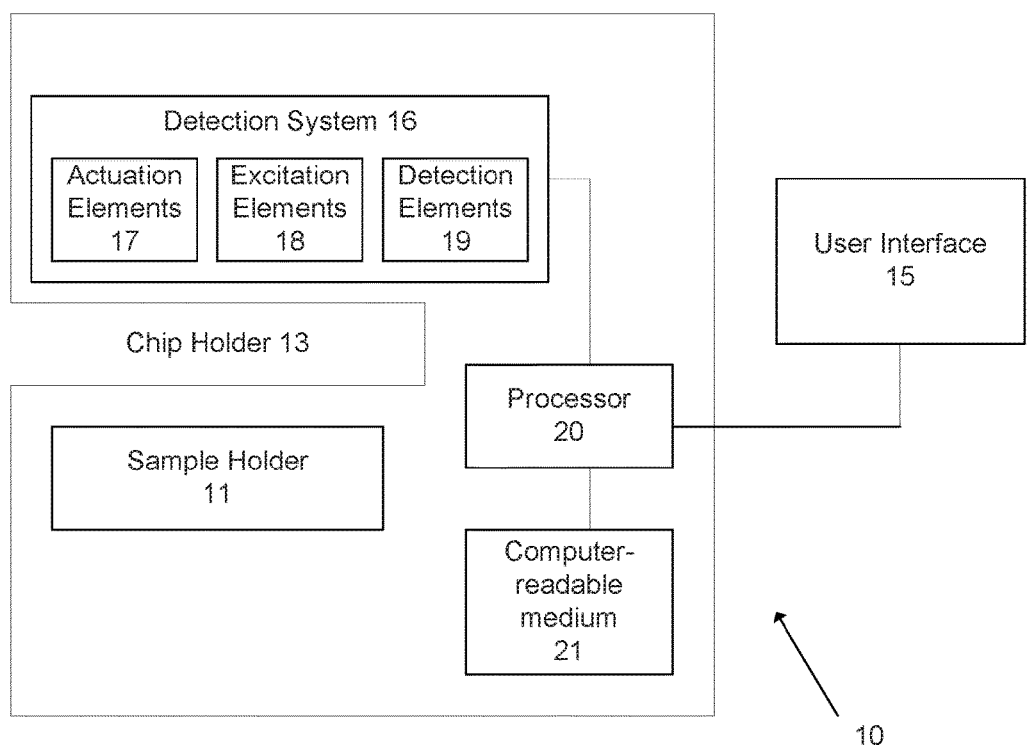
FIG. 1B is a schematic view of the embodiment of FIG. 1A.

FIG. 1B shows a schematic view of the components of the system 10. The system includes a detection system 16, which performs the tasks associated with assaying samples and collecting data. Generally, the detection system 16 comprises actuation elements 17, excitation elements 18, and detection elements 19. The actuation elements 17 interact with the microfluidic chip in various ways to initiate and direct the flow of a sample and assay reagents in the chip. The excitation elements 18 generally include a radiation source of some kind, such as a laser, which is used to illuminate a sample a cause it to emit a detectable signal. The detection elements 19 collect and measure the signal emitted from the excited sample.

The detection system 16 is in communication with a processor 20. The processor 20 executes instructions for processing the output of the detection system 16 and instructions to provide control signals to the detection system to perform assays and otherwise govern its operation. The processor performs calculations specific to the analysis performed by the detection system 16, and numerous other calculations as needed by the user. The computer readable medium 21 stores the instructions utilized by the system and executed by the processor 20. The computer readable medium 21 also stores data associated with the assays performed by the system, including parameters to be applied to perform the assay, assay result data, and any other related information. The medium 21 can take the form of any well-known data storage device compatible with the system and processor requirements.

The processor 20 communicates with the user interface 15, which, in the embodiment of FIG. 1A, is a touch-sensitive display monitor. The processor executes instructions to display data outputs and prompts for the user and also receives user inputs via the interface 15.

Figure 2A:
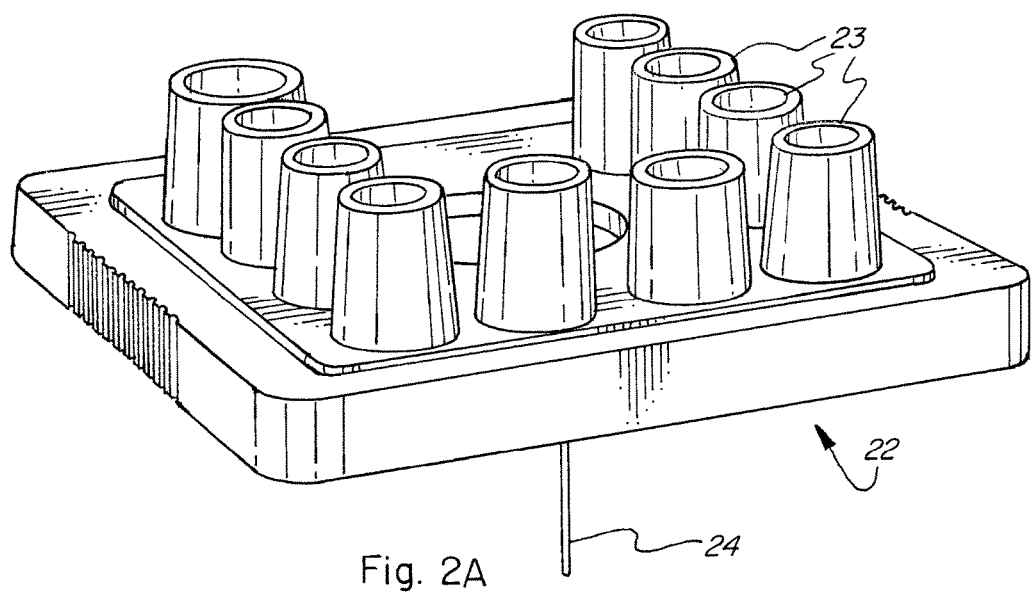
FIG. 2A is a perspective view of a microfluidic chip for use with the embodiment of FIG. 1A.
Figure 2B:
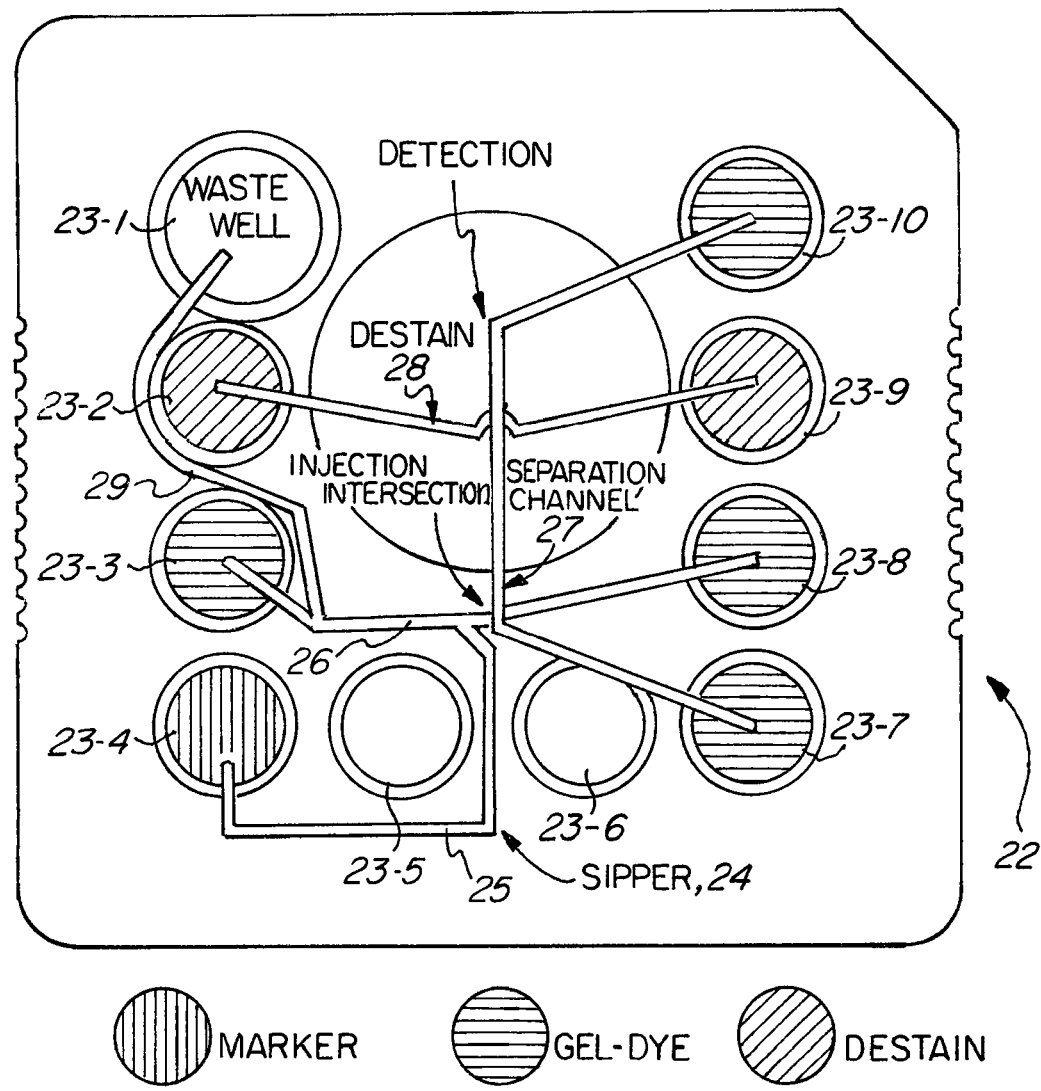
FIG. 2B is a schematic view of the chip of FIG. 2A.

FIGS. 2A and 2B show an exemplary embodiment of a microfluidic chip 22 for use with systems according to the present technology. The chip 22, sometimes referred to as a cartridge, includes a plurality of wells 23 and a sipper 24. The sipper 24 and the wells 23 are linked by a plurality of channels. The wells 23 are used to hold reagents for use in the assay of the sample. FIG. 2B shows a schematic view of a chip 22. The chip 22 includes ten wells 23: a marker well 23-4, four wells that contain a solution of gel, dye, and, in some embodiments, a surfactant such as sodium dodecyl sulfate (SDS) 23-3, 23-7, 23-8, and 23-10, two wells that contain a destain solution, such as gel without dye or SDS 23-2 and 23-9, a waste well 23-1, and two spare wells 23-5 and 23-6. The wells are linked by a network of microfluidic channels. A first channel 25 links the marker well 23-4 to the sipper 24. A second channel 26 is linked to the first channel 25 and connects gel/dye wells 23-3 and 23-8. A third channel 27 is connected to the first and second channels and also links gel/dye wells 23-7 and 23-10. A fourth channel 28 is connected to the third channel 27 and links destain wells 23-2 and 23-9. Finally, a fifth channel 29 links the waste well 23-1 to the second channel 26.

In a typical sample analysis procedure, the chip 22 is prepared with the necessary reagents and then loaded into the chip holder 13. In some embodiments, the microfluidic chip 22 is reusable such that it can be loaded with reagents for a series of assays on a series of samples, cleaned, and then reloaded with reagents for another series of assays. This process can be repeated hundreds, and sometimes thousands, of times. In other embodiments, the chip 22 is considered single use, in which case it is discarded after a one or a series of test runs.

Figure 3:
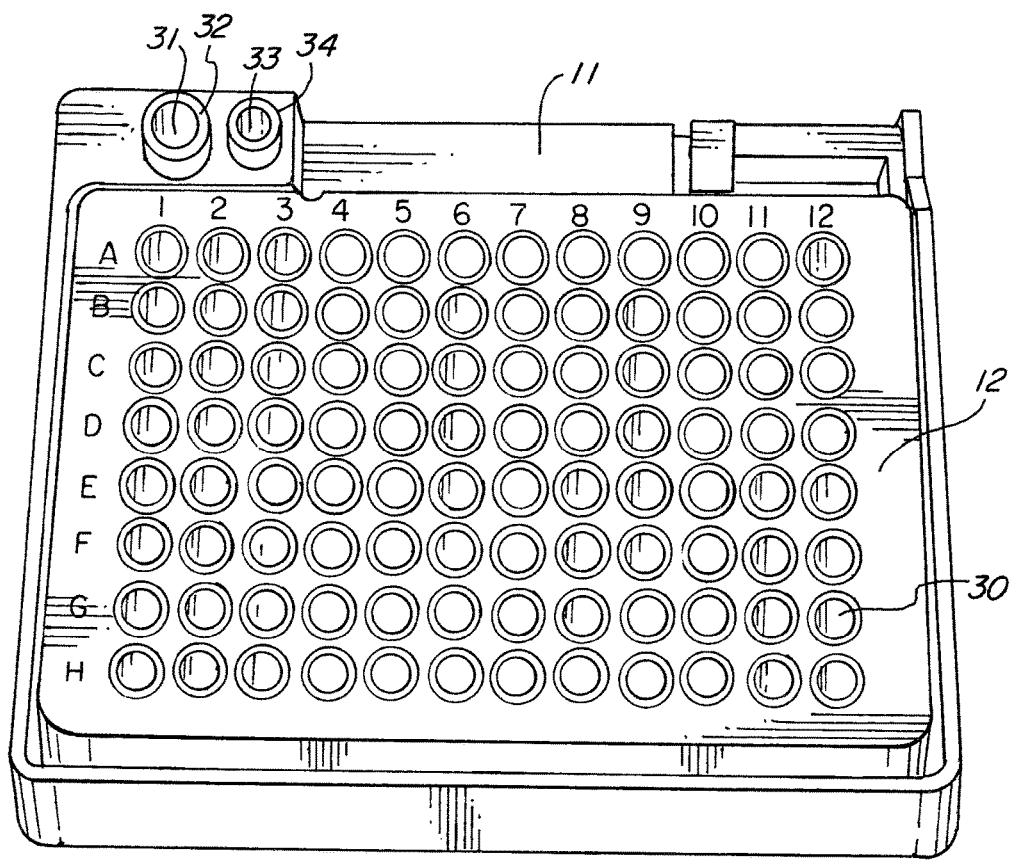
FIG. 3 is a perspective view of a sample plate for use with the embodiment of FIG. 1A.

FIG. 3 shows an exemplary embodiment of a sample plate 12 for use with systems according to the present technology. The sample plate 12 includes a plurality of sample wells in a grid formation, each well having a row letter (A-H) and column number (1-12) associated with it. The plate 12 shown in FIG. 3 has 96 wells, but other embodiments use plates that have any number of sample wells. The plate 12 is shown in FIG. 3 during the process of its being loaded into the sample holder 11 of the system 10. In this embodiment, the holder 11 is in the form of a drawer or movable tray that slides in and out of the main housing of the system 10. The holder 11 includes a buffer well 31 for holding a buffer tube 32, which typically contains a buffer solution. The holder also includes a ladder well 33 for holding a ladder tube 34, which typically contains a ladder sample. Ladder samples are well known standard material samples for comparison with test samples, calibration, etc.

The system 10 is used for a number of different sample assays, among them are protein characterization and DNA/RNA quantification. A typical assay is performed as follows: First, the gel/dye, and in this embodiment, SDS, solution of wells 23-3, 23-7, 23-8, and 23-10 is distributed through the third channel 27, which is also referred to as the separation channel, and second channel 26. This is accomplished by, for example, using well actuation elements to apply pressure to push the gel/dye/SDS solution into the channels. Such a vacuum pressure is applied, in some embodiments, to wells 23-2, 23-7, 23-8, and 23-10. Then, a sample, such as proteins, is brought onto the chip 22 directly from a microtiter plate, such as the sample plate 12, via the capillary sipper 24. This is achieved in some embodiments by activating an actuation element associated with waste well 23-1. In the embodiment shown, the actuation element applies a vacuum at the well 23-1, which exerts a suction force to move a sample up the sipper and onto the chip 22. In other embodiments, the actuation elements may apply other types of forces, such as an electrical force, to move the sample. The system 10 also includes actuation elements that move the chip 22 and/or sample plate 12 relative to one another so that the sipper engages with the desired sample well.

Next, once the sample reaches the chip, it is mixed with marker from well 23-4. Actuation elements associated with well 23-4 cause the marker to mix with the sample in some embodiments and, in other embodiments, the vacuum applied to well 23-1 to draw the sample to the chip will also draw the marker solution from well 23-1. In some embodiments, the marker material includes internal DNA markers.

The sample is then loaded into the gel/dye/SDS solution. Actuation elements in the detection system apply a voltage and electrical current to the wells 23-3 and 23-8, which causes a "loading current" that moves a plug of the sample toward well 23-8. Voltages and currents are then applied to wells 23-7 and 23-10 to cause an "injection current" that injects a small plug of the sample into the separation channel. In some embodiments, most of the wells are associated with one or more actuation elements in the system that apply a voltage and electrical current to the well. The applied voltage and current controls the flow of the sample through the microfluidic channels. In some embodiments, the system 10 permits users to adjust the voltage or electrical current applied to each well, or both, in order to adjust the flow.

Once the plug of sample has been injected into the separation channel, a voltage and current is applied to begin the electrophoresis process. The gel/in wells 23-7 and 23-10 is a sieving matrix, such as, in some embodiments, a low viscosity matrix of entangled polymer. The dye is a fluorescent dye. The voltage and current applied to the wells 23-7 and 23-10 causes the sample to be electrokinetically moved along the separation channel 27, through the gel/SDS/dye solution.

As the sample, for example, a protein-SDS complex along with free SDS micelles, moves through the separation channel 27 it is immediately stained by the dye component present in the sieving matrix. At the end of the separation channel 27, the sample is diluted by a diffusion process to reduce the SDS concentration below its critical micelle concentration. This is intended to reduce the background fluorescence so that protein-SDS-dye complexes can be detected. This is accomplished by actuation elements that apply a voltage to wells 23-2 and 23-9 (containing destain material, such as gel without SDS or dye) to cause current to flow into both sides of the separation channel. The dilution step, referred to as destaining, is accomplished as the electrical fields force the protein-SDS complexes and the free SDS micelles into the center of channel 27; diffusion of SDS toward the sides of channel 27 brings the SDS below critical micelle concentration.

The sieving matrix causes proteins of different types to separate under the force of the electric field applied to wells 23-7 and 23-10. Because different proteins have different sizes, they travel at different rates through the sieving matrix. Thus, the different types of proteins contained in a sample will be separated and organized by size as a result of the sieving matrix and applied electrical field.

The destained sample then moves through the detection point of the separation channel 27 where it is illuminated by an excitation light. This causes the dyed sample to fluoresce, the emissions of which are recorded by the detection elements of the detection system. By the time the proteins are illuminated by the excitation light, they have been separated from each other and sorted by size. The detection elements 19 collect the radiation from the illuminated sample and send this data to the processor 20. The processor 20 can output this data to the user in a number of formats, including in the form of an electropherogram or a virtual gel view for visual comparison with a ladder sample.

In most embodiments, the system 10 is designed to execute the steps of the assay with minimal user inputs. The user may be required to select the type of assay to run, to specify certain analysis parameters, and to select the format of the result data, but many of the tasks associated with an assay will be automated. In many embodiments, the software instructions that govern the performance of the assay are stored in the computer-readable medium and executed by the processor. These instructions are sometimes referred to as a "script." In some embodiments, a measurement system such as system 10 will include a number of default scripts for running a number of common assays. The default scripts will have preloaded values for many of the necessary analysis parameters and will prompt the user for values for other analysis parameters.

For each type of microfluidics assay, there are numerous factors and parameters that determine the results achieved. Fluctuations in these factors and parameters—even when small—can cause unexpected and unwanted variation in the results. These fluctuations can cause problems when, for example, the same assay on the same sample is performed using two different chips of the same design, or in two different systems of the same type, but different results are achieved for each assay. Variations in the results of such tests can reduce the perceived reliability, usefulness, and value of a measurement system.

Traditional calibration techniques can help make results consistent, but have little or no effect on many of the test parameters that are critical to any sample analysis using microfluidics. Many calibration techniques adjust measured results according to a known error or characteristic of a measurement device. For example, in U.S. Pat. No. 7,888, 125 to Gibbons et al., the inventors describe a method of calibrating fluidic devices intended to improve the calibration of microfluidic devices. In that patent, a microfluidic device is used to perform assays on calibration samples. The results of these calibration assays are compared to the results of calibration performed by the manufacturer of the microfluidic device at the factory. This comparison yields a calibration factor to be applied to the signal results obtained during use of that fluidic device.

The calibration method of U.S. Pat. No. 7,888,125 and other known calibration methods, however, will not address numerous parameters that can affect the results of microfluidic assays. As just one example, the method of U.S. Pat. No. 7,888,125 cannot account for variations in the dyes and other reagents utilized with a microfluidic device. The present technology, on the other hand, employs smart software to reduce variability in measured signals by adjusting the operating conditions—or analysis parameters—based on measured signals of previous sample runs. Examples of measured signals include the fluorescence reading from biomolecules (like proteins or other molecules) and measured currents or voltages applied or found in the microfluidic chip.

Figure 4:
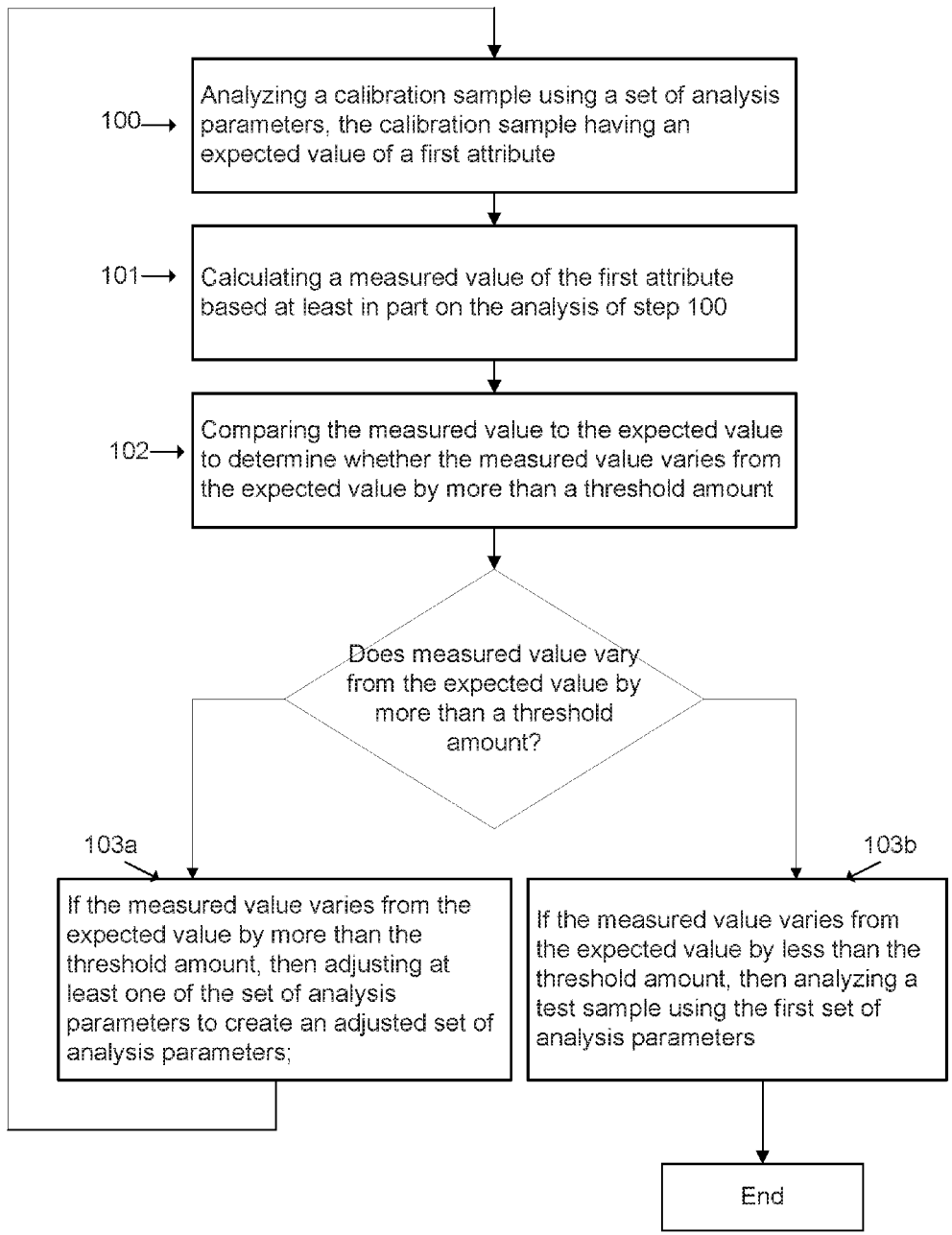
FIG. 4 is a flow chart depicting a method according to an embodiment of the present technology.

FIG. 4 is a flow chart depicting a method according to a first embodiment of the present technology. First, a calibration sample is analyzed using a set of analysis parameters, where the sample has an expected value of a first attribute at step 100. Next, at step 101, a measured value of the first attribute is calculated based at least in part on the analysis of step 100. Then, at step 102, the measured value is compared to the expected value to determine whether the measured value varies from the expected value by more than a threshold amount. If the measured value varies from the expected value by more than the threshold amount, then, at step 103*a*, at least one of the set of analysis parameters is adjusted to create an adjusted set of analysis parameters and steps 100-103 are performed iteratively using the adjusted set of analysis parameters until the measured value varies from the expected value by less than the threshold amount. If the measured value varies from the expected value by less than the threshold amount, then, at step 103*b*, a test sample is analyzed using the first set of analysis parameters.

The first embodiment has been advantageously applied to the process of destaining a protein sample during a protein separation assay. By way of background, fluctuations in the parameters associated with the destain process can cause significant run-to-run variation. In certain protein separation assays, the protein measurement signal is achieved by decorating the proteins using SDS (sodium dodecyl sulfate) and a hydrophobic dye. Sometimes, this process also creates a lot of free SDS micelles (an entity which is formed by many SDS molecules) that are not attached to the proteins, and which are fluorescent. An excessive concentration of SDS micelles will produce a large background fluorescence signal that can mask the protein measurement signal.

Destaining is intended to lower the SDS micelle concentration to improve the background fluorescence signal to allow better detection of stained proteins. SDS micelles can be destroyed by lowering the concentration of SDS via dilution with non-SDS ions. The free micelles are broken up when the SDS concentration falls below a critical micellar concentration or "CMC." The degree of dilution, and thus destain, is governed by the ratio of the current applied to the chip wells without SDS and dye (e.g., the destain wells 23-2 and 23-9) and to the current applied to wells with the SDS and dye (e.g. wells 23-7 and 23-10) and that acts on the protein sample. The voltage or the current, or both, applied to these wells can be adjusted to control the flow of SDS micelles and protein-SDS complexes. It is more advantageous in some embodiments to control the current or a combination of the voltage and the current. This is because the electric current is directly proportional to the flow rate in situations where the material flow is purely electrokinetic, which is the case in most microfluidic measurement systems. In many embodiments, therefore, the destain ratio is a ratio of applied currents, such that the amount of destain is adjusted by adjusting the applied currents relative to each other. In other embodiments, adjustments to the destain ratio are achieved by adjusting the applied voltages, or a combination of the applied voltages and currents.

There are a variety of parameters that determine the CMC, including: the concentration of buffer components, the concentration of SDS monomer, the type and concentration of dye, and undesired additives that may affect buffer quality. The CMC can vary due to variability in any of these parameters. Similarly, the CMC can vary from run to run due to variability in reagents, variability in resistance in the channels on the chip, and differences in sample preparation workflow. In some cases, a pre-set or default current ratio intended to accomplish destain may not bring the SDS concentration sufficiently below CMC for a variety of reasons, in which case the background signal would be undesirably high. That means free micelles carrying dye molecules produce a large background signal and that can mask the fluorescent measurement signal associated with proteins. The result is an inaccurate protein measurement signal, as relevant protein peaks disappear in the excessive background signal.

The destain current ratio also affects the diffusion of SDS micelles from the sample stream to the destain stream. In addition to SDS and dye concentration, discussed above, the degree of protein staining and destaining is influenced by this diffusion of SDS micelles. The diffusion of SDS micelles is controlled by the diffusion coefficient of SDS micelles and the diffusion distance. The diffusion distance can be altered by changing the current ratio between the sample stream and destaining streams. When applying higher destaining current, the sample stream becomes more narrow and therefore the SDS micelles diffuse faster and the destaining is more efficient. Another variable determining the destaining efficiency is the diffusion time. When labeled proteins pass through the optic detector, the fluorescent signal is recorded as a peak profile from background (extra micelles that carry the dye), which is further analyzed to identify protein size and concentration. While the proteins and SDS micelles are migrating along the separation channel towards the detector, destaining is happening by the diffusion of those molecules across the separation channel. The electric field and distance from the destain channel(s) to the detector determines the time of diffusion thus the efficiency of destain.

Thus, a fixed destain current ratio may cause different background and protein peak signals due to slight variations in CMC of the SDS micelles and in the diffusion distance and time. This fixed destain current is typically the default destain current that is part of the default script for the protein separation assay. According to the present technology, run-to-run variation in the protein signal can be avoided by optimizing the destain current ratio prior to the test sample runs.

In the context of a destaining process, the method of FIG. 4 is applied with steps specific to the destain process. In this embodiment, the destain ratio is among the set of analysis parameters. In some embodiments, the first attribute is the percent purity of a material (such as a protein) in the sample. The destain ratio is, as described above, the ratio of an amount of voltage and/or electric current to be applied to a well containing the destain material to an amount of voltage and/or electric current to be applied to draw the sample through the sieving matrix.

Figure 5:
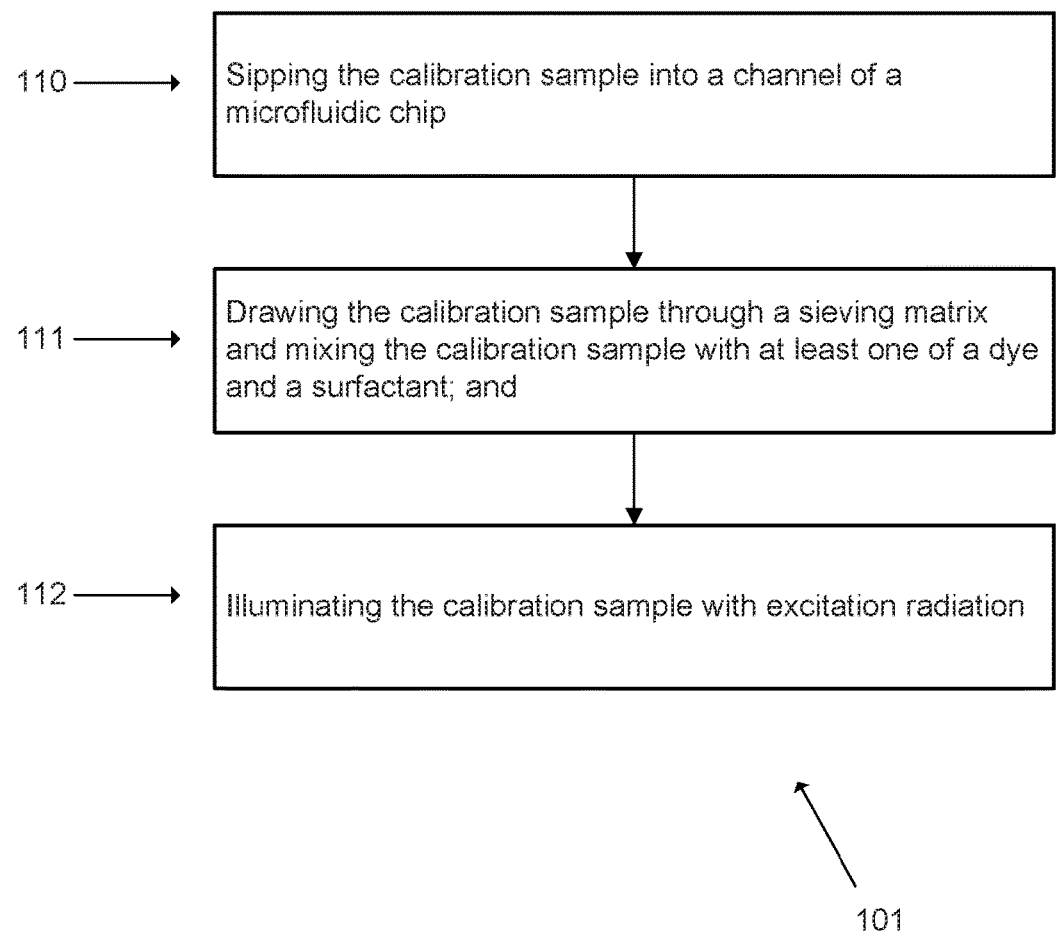
FIG. 5 is a flow chart depicting additional steps of an embodiment of the method of FIG. 4.

To begin analysis of a calibration sample, a microfluidic chip is prepared for an assay of one or more samples having the first attribute. The sample plate is prepared with the one or more samples to be assayed, along with a ladder sample and the calibration sample. In this embodiment, the step 101 of analyzing a calibration sample using a set of analysis parameters includes the steps of: sipping the calibration sample into a channel of the microfluidic chip (110), drawing the calibration sample through a sieving matrix and mixing the calibration sample with at least one of a dye and a surfactant (111); and illuminating the calibration sample with excitation radiation (112). This process is depicted in FIG. 5.

Figure 6:
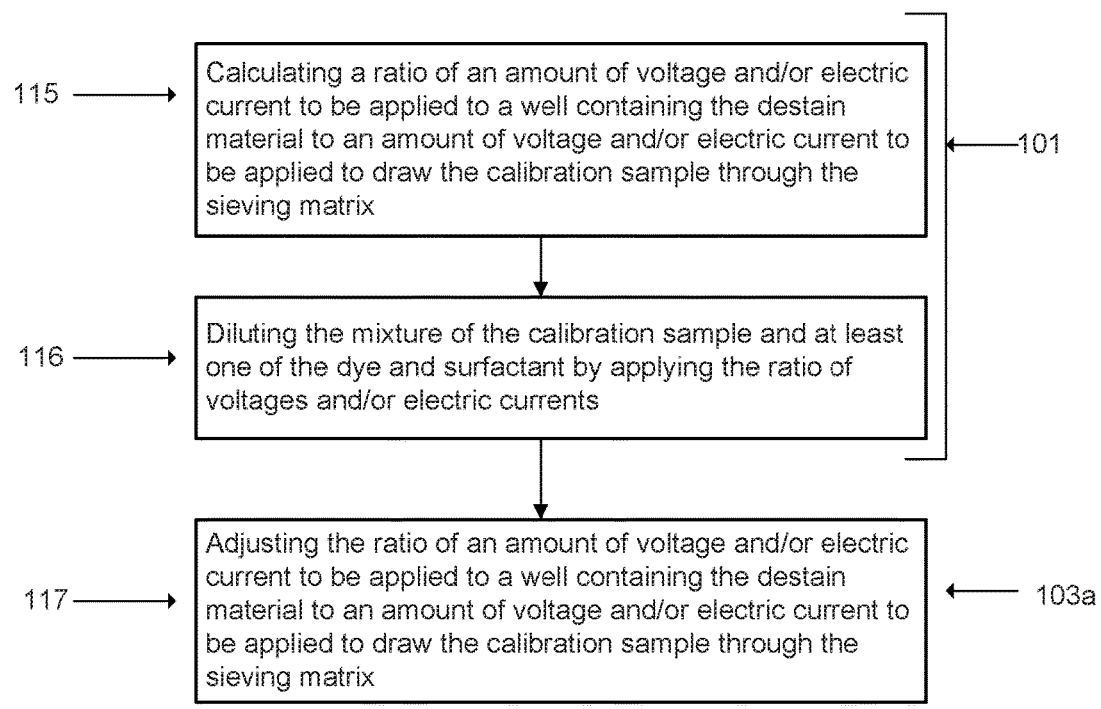
FIG. 6 is a flow chart depicting additional steps of the embodiment of the method of FIG. 5.

The analysis of the calibration sample according to step 101 in the context of the destain process also includes the steps, shown in FIG. 6, of: calculating a ratio of an amount of voltage and/or electric current to be applied to a well containing a destain material to an amount of voltage and/or electric current to be applied to draw the calibration sample through the sieving matrix (115); and diluting the mixture of the calibration sample and at least one of the dye and surfactant by applying the ratio of voltages and/or electric currents (116).

The measured value is compared at step 102 to the expected value of the first attribute to determine if the measured value varies from the expected value by more than a threshold amount. This is done in some embodiments by subtracting the measured value from the expected value and taking the absolute value of the result. The threshold amount will vary according to the type of assay being performed and the purpose of the assay. In one embodiment, the threshold is about 5% of the expected value, so that if the measured value is different than the expected value by an amount that is less than about 5% of the expected value, then the measured value varies from the expected value by less than a threshold amount. In other embodiments, the threshold amount is about 4% of the expected value, about 3% of the expected value, about 2% of the expected value, about 1% of the expected value, or about 0.5% of the expected value. Other threshold amounts are used in other embodiments according to the assay to be performed and/or the user's preferences.

If the measured value varies from the expected value by more than the threshold amount, then the destain ratio is adjusted so that the set of analysis parameters is now an adjusted set of analysis parameters at step 103*a*. This can be accomplished by adjusting the voltages and/or electric currents applied to the destain wells, the gel/dye/SDS wells, or both pursuant to step 117 in FIG. 6. In one advantageous embodiment, the destain ratio is adjusted by a set increment of 0.25. In other embodiments, other parameters of the set of analysis parameters are adjusted. The calibration sample is then assayed using the adjusted set of analysis parameters, which includes the adjusted destain ratio. The measured value of the first attribute (here the percent purity) is calculated again and compared to the expected value. This process is repeated iteratively until the measured value varies from the expected value by less than the threshold amount.

Once the destain ratio that provides a measured value close enough to the expected value has been determined, it is selected for use with the remaining sample assays to be performed with that fluidic chip at step 103*b*. The final selected destain ratio replaces the original destain ratio in the script for the protein separation assay and forms part of the final adjusted set of analysis parameters that is then used to assay the user's actual test samples. As mentioned above, in other embodiments, adjustment of the degree of destain by the system is accomplished by changing the applied voltage or both the applied voltage and the applied current instead of only the applied current.

In some embodiments, preprocessing steps are undertaken to determine a baseline destain current ratio for use at the start of the optimization process. In some embodiments, the baseline destain ratio is provided as part of the default set of analysis parameters, while in other embodiments, the system includes a script for calculating a baseline destain ratio for use with a chip prepared to perform a series of assays. The following describes the steps necessary to calculate the baseline destain ratio, which are typically executed by software executing in at least one processor in the system 10.

In general, the calculation of the baseline ratio is based on the electric resistance and expected mobility for a standard material for at least one channel on the microfluidic chip. More specifically, first, a series of sips from the ladder sample are taken by the chip. These ladder sample sips are then analyzed to determine the migration time of a given material (such as 120 kDa protein) in the sample along with the associated current through those sips. The conductivity of the channels of the chip is then determined. Using this data, calculations are made to determine the mobility of a known material (such as 120 kDa protein), the resistances of the channels, and the electrical currents to apply to the wells of the chip for the calculated migration time. Based on these calculations, a maximum initial destain ratio for the chip in use can then be calculated.

Next, using a calibration sample, two test runs are performed to obtain data on the first attribute, which has a known, expected value. The calibration sample is provided with a known expected value of percent purity. The calibration sample is sipped from the sample plate (e.g., from sample well A1) via the sipper 24. The sample is then mixed with a marker, and drawn through the separation channel (third channel 27), which contains the sieving matrix (the gel/dye solution). The sample is then illuminated with excitation radiation from the laser, and the resulting fluorescent emissions of the sample are recorded.

A first measurement run with the calibration sample uses the maximum initial destain ratio calculated above using the ladder samples, and a second run uses a minimum initial destain ratio. The minimum initial destain ratio may be provided as a default parameter. As described above, the destain ratio is the ratio of current (or voltage) applied to the destain wells 23-2 and 23-9 to the current (or voltage) applied to draw the sample through the separation channel (wells 23-7 and 23-10). Using the results of these two runs, the system calculates the baseline destain ratio that is predicted to give the expected percent purity, including the respective voltages and/or currents to apply to the destain wells (23-2 and 23-9) and the wells 23-10 and 23-7 to achieve the desired degree of initial destain.

Once the baseline destain ratio has been calculated, the optimization process described above can begin using this baseline destain in the set of analysis parameters to be applied to the calibration sample.

In most embodiments of the present technology, the various steps of the foregoing process are undertaken by software. This includes the various calculations and control inputs for the actuation elements of the detection system. The system software will prompt the user for input at various steps along the way. In some embodiments of the technology, user input will be solicited by the system for selecting the threshold amount discussed above, the amount of incremental change to apply to the destain ratio during optimization of the ratio, and confirmation to initiate each successive assay and one or more steps of each assay. The user is also prompted to select the format in which he or she wishes to view assay data, and which of multiple data manipulation tasks he or she wishes the system to perform.

By optimizing the destain ratio for a particular chip with a particular set of reagents to obtain a fluorescence signal that provides the expected results, the user will obtain consistent results that can be reliably compared to results obtained using the same assay on a second chip (assuming the same optimization process is performed on the second chip). The above iterative optimization process is advantageously employed with respect to a variety of parameters associated with the assay process. These include: laser power, focus position, injection volume, dye fluorescence, the concentrations of reagents, and others. In addition to manipulating current ratios, other operating and controlling variables of microfluidic chips, such as imposed voltages and/or currents and/or pressures in supply wells, detector position, or imposed times of various steps can be changed, singly or in combination.

In a second embodiment of the present technology, the concentration of reagents mixed with the sample is optimized using a feedback algorithm similar to the process described above. The degree of dilution of a sample in reagents in a microfluidic network channel can be controlled by applying currents and/or voltage to two wells containing different concentrations (one high and one low) of the reagents. The exact concentration of a specific reagent can be achieved by tuning appropriate currents from the high concentration and low concentration wells. In the context of the present technology, data obtained from analysis of a calibration standard can be used to optimize fluorescent signal levels through adjustment of the relative voltage and/or current settings of reagent wells containing high and low concentrations of, for example, SDS and dye. Once the appropriate voltage or current settings are determined, the default settings are replaced with the adjusted or optimized settings.

Figure 7:
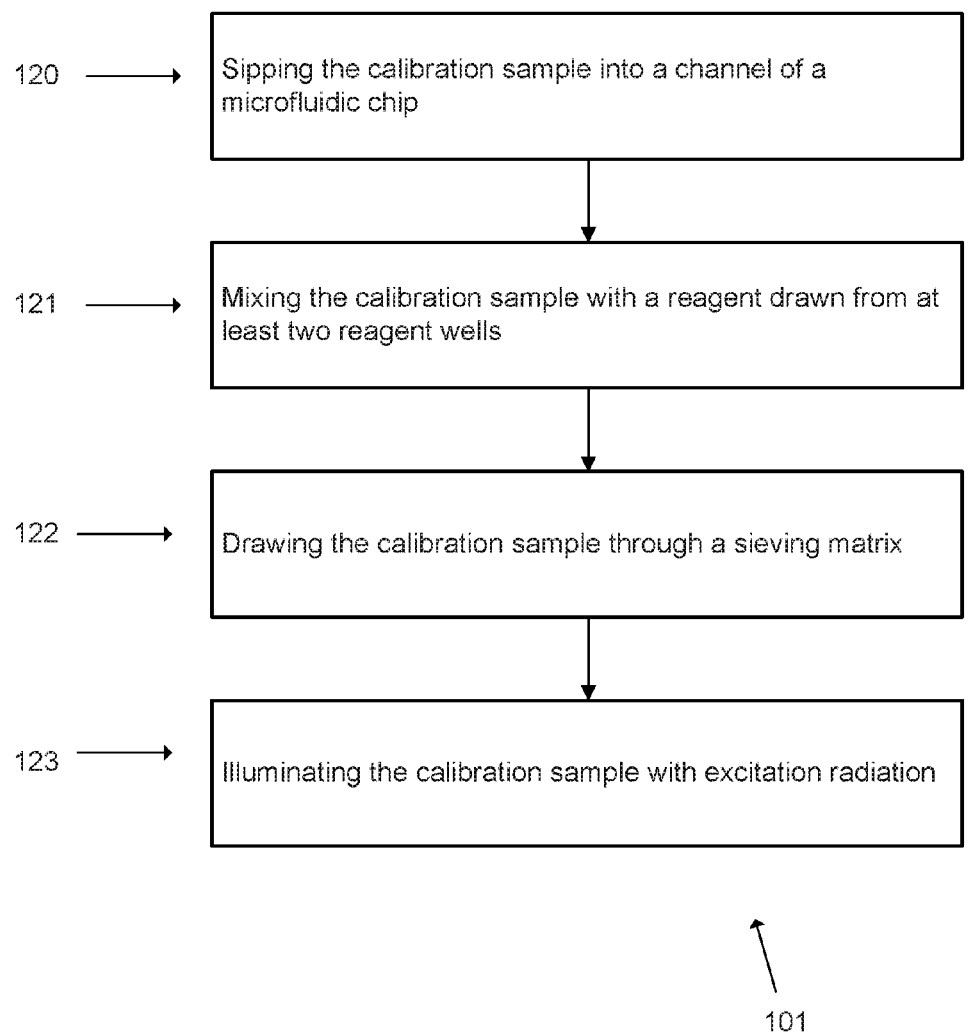
FIG. 7 is a flow chart depicting additional steps of a second embodiment of the method of FIG. 4.
Figure 8:
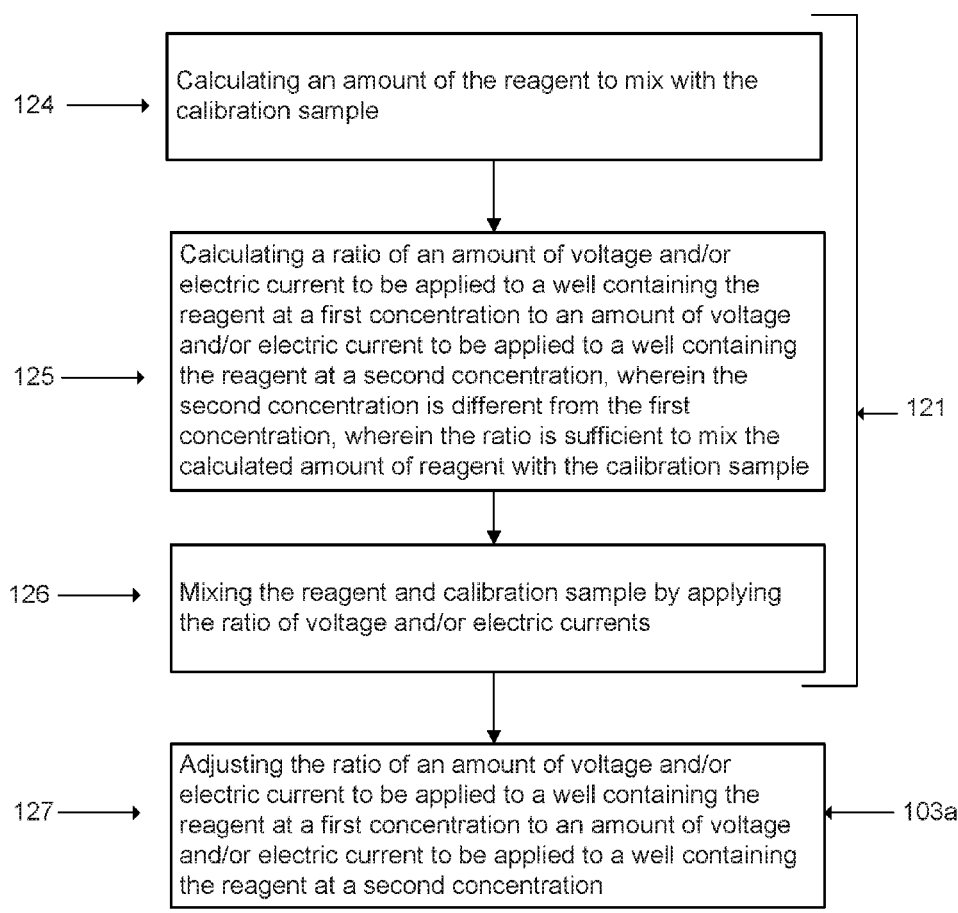
FIG. 8 is a flow chart depicting additional steps of the embodiment of the method of FIG. 7.

FIG. 7 shows the steps that comprise step 101 in the context of optimizing reagent concentration. In this embodiment, a calibration sample is analyzed using a set of analysis parameters that includes a ratio of currents to be applied to a high-concentration reagent well and a low-concentration reagent well, respectively. The calibration sample again has a first attribute that has an expected value. The analysis involves: sipping the calibration sample into a channel of a microfluidic chip (120); mixing the calibration sample with a reagent drawn from at least two reagent wells (121); drawing the calibration sample through a sieving matrix (122); and Illuminating the calibration sample with excitation radiation (123).

In some embodiments, the step 121 further comprises the steps of: calculating an amount of the reagent to mix with the calibration sample (124); calculating a ratio of an amount of voltage and/or electric current to be applied to a well containing the reagent at a first concentration to an amount of voltage and/or electric current to be applied to a well containing the reagent at a second concentration, wherein the second concentration is different from the first concentration, wherein the ratio is sufficient to mix the calculated amount of reagent with the calibration sample (125); and mixing the reagent and calibration sample by applying the ratio of voltage and/or electric currents (126).

The results of the analysis include a measured value of the first attribute, which is then compared to the expected value. The comparison includes analysis of the fluorescence signal produced by the selected reagent concentration. If the fluorescence signal does not produce a measured value that is sufficiently similar to the expected value, then the currents applied to the reagent wells are adjusted and another calibration sample analysis is performed (see step 127). Again, this process is performed iteratively as many times as necessary until the desired measured value is obtained (see step 103a). At that point, the adjusted currents are stored as an adjusted set of analysis parameters and applied to the test samples (step 103b). As in the embodiment described above, the method uses the history of sample runs on a microfluidic chip to adjust the operating conditions of the chip. This produces better and more consistent results by minimizing the effect of errors in the reagents and chip conditions.

The manner in which analysis parameters are altered and tested against standardized samples is implemented in several different ways in different embodiments of the technology. Specific test scripts can be implemented, and/or iterative tests of several default scripts with incremental changes in specific parameters can be implemented. In addition to manipulating current ratios, other operating/controlling variables of microfluidic chips such as imposed voltages and/or currents and/or pressures in supply wells, detector position, or imposed times of various steps can be changed, singly or in combination. Standards against which a specific response is measured can be changed according to the assay type, sample type, and performance attribute to be optimized. Standards may be tested independently for per-run optimization of operating parameters or may be mixed with each sample for per-sample optimization. In the case of per-sample optimization, each sample would be tested multiple times until the optimized parameters are identified and applied for the actual sample analysis. Presentation to the user and transparency of the steps, tests, data, and/or analyses used during optimization will be controlled through the software display and may vary according to the goals of the specific assay.

Accordingly, the present technology provides systems and methods for improving the run-to-run consistency of measurement results generated by, for example, a microfluidic measurement system. The present technology, which is advantageously implemented via software that may be preloaded into a measurement system or purchased by a user to upgrade his or her pre-existing system, allows a user to accommodate fluctuation in the analysis parameters that can cause significant run-to-run variation.

Although the technology has been described with reference to particular embodiments and arrangements of parts, features and the like, these are not intended to exhaust all possible embodiments, arrangements, or features, and indeed many other modifications and variations will be ascertainable to those of skill in the art.

What is claimed is:

1. A method for analyzing a sample, comprising the steps of:
   A) for a calibration sample having a first attribute with an expected value, analyzing the calibration sample using a set of analysis parameters;
   B) calculating a measured value of the first attribute of the calibration sample based at least in part on the analysis of step A);
   C) comparing the measured value to the expected value to determine whether the measured value varies from the expected value by more than a threshold amount;
   D) if the measured value varies from the expected value by more than the threshold amount, then
      1) adjusting at least one of the set of analysis parameters to create an adjusted set of analysis parameters;
      2) performing steps A)-D) iteratively using the adjusted set of analysis parameters until the measured value varies from the expected value by less than the threshold amount; and
   E) if the measured value varies from the expected value by less than the threshold amount, then analyzing a test sample using the first set of analysis parameters.

2. The method of claim 1, wherein the step of A) analyzing a calibration sample further comprises the steps of:
   1) sipping the calibration sample into a channel of a microfluidic chip;
   2) drawing the calibration sample through a sieving matrix and mixing the calibration sample with at least one of a dye and a surfactant; and
   3) illuminating the calibration sample with excitation radiation.

3. The method of claim 2, wherein the calibration sample comprises a protein and wherein step A) of analyzing a calibration sample further comprises the steps of:
   4) calculating a ratio of an amount of voltage and/or electric current to be applied to a well containing a destain material to an amount of voltage and/or electric current to be applied to draw the calibration sample through the sieving matrix; and
   5) diluting the mixture of the calibration sample and at least one of the dye and surfactant by applying the ratio of voltages and/or electric currents.

4. The method of claim 3, wherein the step D)1) of adjusting at least one of the set of analysis parameters further comprises adjusting the ratio of an amount of voltage and/or electric current to be applied to a well containing the destain material to an amount of voltage and/or electric current to be applied to draw the calibration sample through the sieving matrix.

5. The method of claim 4, wherein the first attribute is the purity of the calibration sample and the expected value is expressed as a percentage, the step C) of comparing the measured value to the expected value further comprises the steps of:
   1) calculating the percent purity of the calibration sample to obtain the measured value; and
   2) subtracting the measured value from the expected value to obtain a value difference.

6. The method of claim 5, wherein the variation between the measured value and the expected value is determined to be below the threshold amount when the absolute value of the value difference is less than about 5% of the expected value.

7. The method of claim 6, wherein the step D)2) of performing steps A)-D) iteratively further comprises the step of:
   i) adjusting the ratio by about 0.25 on each iteration of the performance of steps A)-D).

8. The method of claim 7, further comprises the step of:
   F) calculating, based on the electric resistance and expected mobility for a standard material for at least one channel on the microfluidic chip, a baseline ratio of an amount of voltage and/or electric current to be applied to a well containing the destain material to an amount of voltage and/or electric current to be applied to draw the calibration sample through the sieving matrix.

9. The method of claim 1, wherein the step of A) analyzing a calibration sample further comprises the steps of:
  1) sipping the calibration sample into a channel of a microfluidic chip;
  2) mixing the calibration sample with a reagent drawn from at least two reagent wells;
  3) drawing the calibration sample through a sieving matrix; and
  4) illuminating the calibration sample with excitation radiation.

10. The method of claim 9, wherein the step A)2) of mixing the calibration sample with a reagent further comprises the steps of:
  a) calculating an amount of the reagent to mix with the calibration sample;
  b) calculating a ratio of an amount of voltage and/or electric current to be applied to a well containing the reagent at a first concentration to an amount of voltage and/or electric current to be applied to a well containing the reagent at a second concentration, wherein the second concentration is different from the first concentration, wherein the ratio is sufficient to mix the calculated amount of reagent with the calibration sample; and
  c) mixing the reagent and calibration sample by applying the ratio of voltage and/or electric currents.

11. The method of claim 10, wherein the step D)1) of adjusting at least one of the set of analysis parameters further comprises adjusting the ratio of an amount of voltage and/or electric current to be applied to a well containing the reagent at a first concentration to an amount of voltage and/or electric current to be applied to a well containing the reagent at a second concentration.

12. A method for analyzing a sample, comprising the steps of:
  A) for a calibration sample having a first attribute with an expected value, analyzing the calibration sample using a set of analysis parameters;
  B) calculating a measured value of the first attribute of the calibration sample based at least in part on the analysis of step A);
  C) comparing the measured value to the expected value to determine whether the measured value varies from the expected value by more than a threshold amount;
  D) if the measured value varies from the expected value by more than the threshold amount, then
    1) adjusting at least one of the set of analysis parameters to create an adjusted set of analysis parameters;
    2) performing steps A)-D) iteratively using the adjusted set of analysis parameters until the measured value varies from the expected value by less than the threshold amount; and
  E) if the measured value varies from the expected value by less than the threshold amount, then analyzing a test sample using the first set of analysis parameters;
  wherein the calibration sample comprises a protein, and wherein the step of A) analyzing a calibration sample comprises the steps of:
    1) sipping the calibration sample into a channel of a microfluidic chip;
    2) drawing the calibration sample through a sieving matrix and mixing the calibration sample with at least one of a dye and a surfactant;
    3) illuminating the calibration sample with excitation radiation;
    4) calculating a ratio of an amount of voltage and/or electric current to be applied to a well containing a destain material to an amount of voltage and/or electric current to be applied to draw the calibration sample through the sieving matrix; and
    5) diluting the mixture of the calibration sample and at least one of the dye and surfactant by applying the ratio of voltages and/or electric currents.

13. The method of claim 12, wherein the step D)1) of adjusting at least one of the set of analysis parameters further comprises adjusting the ratio of an amount of voltage and/or electric current to be applied to a well containing the destain material to an amount of voltage and/or electric current to be applied to draw the calibration sample through the sieving matrix.

14. The method of claim 13, wherein the first attribute is the purity of the calibration sample and the expected value is expressed as a percentage, the step C) of comparing the measured value to the expected value further comprises the steps of:
  1) calculating the percent purity of the calibration sample to obtain the measured value; and
  2) subtracting the measured value from the expected value to obtain a value difference.

15. The method of claim 14, wherein the variation between the measured value and the expected value is determined to be below the threshold amount when the absolute value of the value difference is less than about 5% of the expected value.

16. The method of claim 15, wherein the step D)2) of performing steps A)-D) iteratively further comprises the step of:
  i) adjusting the ratio by about 0.25 on each iteration of the performance of steps A)-D).

17. The method of claim 16, further comprises the step of:
  F) calculating, based on the electric resistance and expected mobility for a standard material for at least one channel on the microfluidic chip, a baseline ratio of an amount of voltage and/or electric current to be applied to a well containing the destain material to an amount of voltage and/or electric current to be applied to draw the calibration sample through the sieving matrix.

18. A method for analyzing a sample, comprising the steps of:
  A) for a calibration sample having a first attribute with an expected value, analyzing the calibration sample using a set of analysis parameters;
  B) calculating a measured value of the first attribute of the calibration sample based at least in part on the analysis of step A);
  C) comparing the measured value to the expected value to determine whether the measured value varies from the expected value by more than a threshold amount;
  D) if the measured value varies from the expected value by more than the threshold amount, then
    1) adjusting at least one of the set of analysis parameters to create an adjusted set of analysis parameters;
    2) performing steps A)-D) iteratively using the adjusted set of analysis parameters until the measured value varies from the expected value by less than the threshold amount; and
  E) if the measured value varies from the expected value by less than the threshold amount, then analyzing a test sample using the first set of analysis parameters;
  wherein the step of A) analyzing a calibration sample further comprises the steps of:
    1) sipping the calibration sample into a channel of a microfluidic chip;

2) mixing the calibration sample with a reagent drawn from at least two reagent wells;
3) drawing the calibration sample through a sieving matrix; and
4) illuminating the calibration sample with excitation radiation; and wherein the step A)2) of mixing the calibration sample with a reagent further comprises the steps of:
a) calculating an amount of the reagent to mix with the calibration sample;
b) calculating a ratio of an amount of voltage and/or electric current to be applied to a well containing the reagent at a first concentration to an amount of voltage and/or electric current to be applied to a well containing the reagent at a second concentration, wherein the second concentration is different from the first concentration, wherein the ratio is sufficient to mix the calculated amount of reagent with the calibration sample; and
c) mixing the reagent and calibration sample by applying the ratio of voltage and/or electric currents.

19. The method of claim 18, wherein the step D)1) of adjusting at least one of the set of analysis parameters further comprises adjusting the ratio of an amount of voltage and/or electric current to be applied to a well containing the reagent at a first concentration to an amount of voltage and/or electric current to be applied to a well containing the reagent at a second concentration.

* * * * *